(12) United States Patent
Badenhorst et al.

(10) Patent No.: US 12,110,534 B2
(45) Date of Patent: Oct. 8, 2024

(54) GENERATION OF SINGLE-STRANDED CIRCULAR DNA TEMPLATES FOR SINGLE MOLECULE SEQUENCING

(71) Applicants: Roche Sequencing Solutions, Inc., Pleasanton, CA (US); Kapa Biosystems, Inc., Wilmington, MA (US)

(72) Inventors: Daleen Badenhorst, Wellington (ZA); Michael S. Berry, Woodstock (ZA); Richard Dannebaum, Pleasant Hill, CA (US); Ashley Hayes, San Francisco, CA (US); Severine Margeridon, Castro Valley, CA (US); Martin Ranik, Kenilworth (ZA); Etienne Slabbert, Stellenbosch (ZA)

(73) Assignees: Roche Sequencing Solutions, Inc., Pleasanton, CA (US); Kapa Biosystems, Inc., Wilmington, MA (US)

( * ) Notice: Subject to any disclaimer, the term of this patent is extended or adjusted under 35 U.S.C. 154(b) by 1105 days.

(21) Appl. No.: 16/945,099

(22) Filed: Jul. 31, 2020

(65) Prior Publication Data
US 2021/0115510 A1   Apr. 22, 2021

Related U.S. Application Data

(63) Continuation of application No. PCT/EP2019/052764, filed on Feb. 5, 2019.

(60) Provisional application No. 62/626,589, filed on Feb. 5, 2018.

(51) Int. Cl.
C12Q 1/6806 (2018.01)
C12Q 1/6869 (2018.01)

(52) U.S. Cl.
CPC .......... *C12Q 1/6806* (2013.01); *C12Q 1/6869* (2013.01); *C12Q 2521/319* (2013.01); *C12Q 2525/155* (2013.01); *C12Q 2525/191* (2013.01); *C12Q 2525/307* (2013.01); *C12Q 2535/122* (2013.01)

(58) Field of Classification Search
None
See application file for complete search history.

(56) References Cited

U.S. PATENT DOCUMENTS

| | | | |
|---|---|---|---|
| 2003/0207279 A1* | 11/2003 | Crothers et al. | C12Q 1/6853 435/6.15 |
| 2004/0265888 A1 | 12/2004 | Horlick | |
| 2009/0280538 A1 | 11/2009 | Patel et al. | |

(Continued)

FOREIGN PATENT DOCUMENTS

| | | |
|---|---|---|
| CN | 105400776 A | 3/2016 |
| EP | 3192877 A1 | 7/2017 |

(Continued)

OTHER PUBLICATIONS

Myllykangas S et al., Targeted sequencing library preparation by genomic DNA circularization, BMC Biotechnology, (2011), pp. 122, vol. 11 Issue 1.

*Primary Examiner* — Kaijiang Zhang
(74) *Attorney, Agent, or Firm* — Eric Grant Lee

(57) ABSTRACT

The invention is a novel method of sequencing nucleic acids involving making and sequencing a library of single stranded circular target nucleic acids.

11 Claims, 8 Drawing Sheets
Specification includes a Sequence Listing.

(56) References Cited

U.S. PATENT DOCUMENTS

2017/0275609 A1* 9/2017 Geng et al. ............ C12N 15/10
2017/0356039 A1   12/2017 Jiang et al.
2018/0044667 A1    2/2018 Geng et al.

FOREIGN PATENT DOCUMENTS

| WO | 94/16090 A1 | 7/1994 | |
|----|----|----|----|
| WO | 01/12855 A2 | 2/2001 | |
| WO | 2009/120372 A2 | 10/2009 | |
| WO | 2011/088573 A1 | 7/2011 | |
| WO | WO2012003374 A2 | 1/2012 | |
| WO | 2012/104261 A1 | 8/2012 | |
| WO | WO2012162267 A2 | 11/2012 | |
| WO | 2013/188840 A1 | 12/2013 | |
| WO | 2014/196863 A1 | 12/2014 | |
| WO | 2015/022359 A1 | 2/2015 | |
| WO | WO-2016040901 A1 * | 3/2016 | ......... C12N 15/1065 |

\* cited by examiner

FIGURE 4
PacBio control
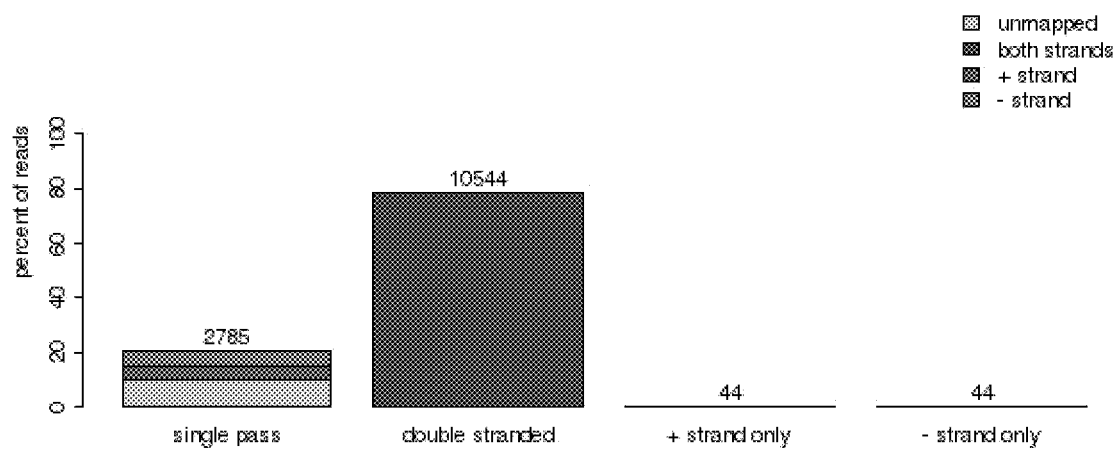
Y-adaptor, non-denatured control
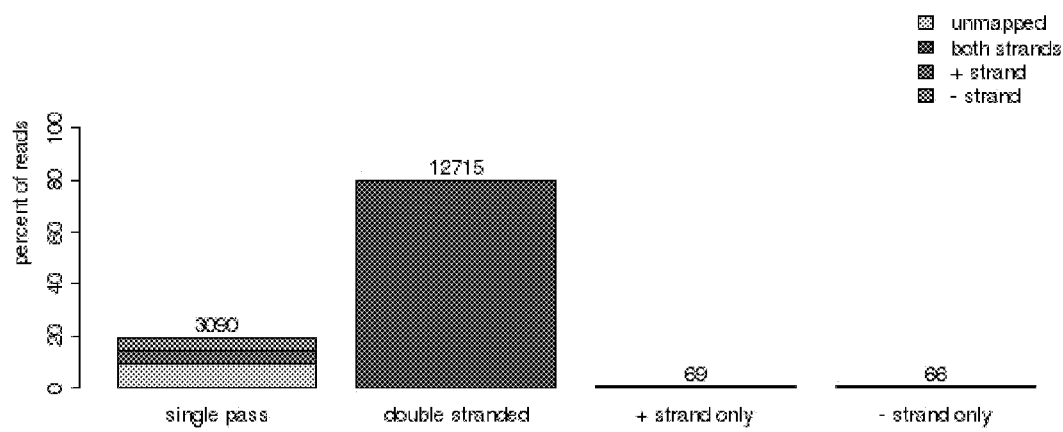

FIGURE 5
Heat-denatured
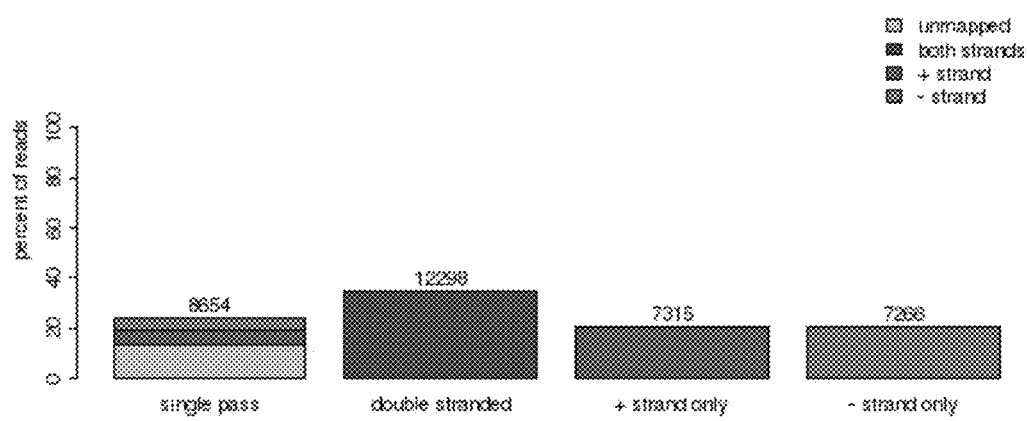
Heat-denatured + SSB
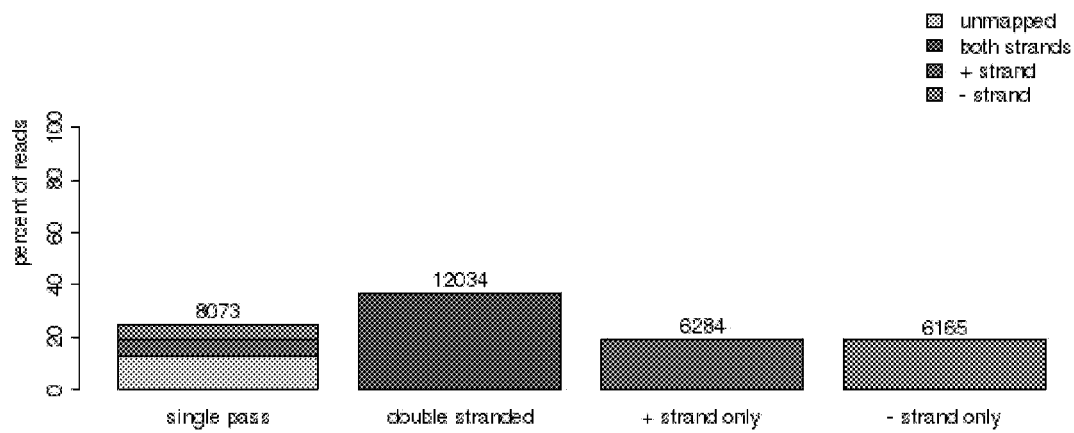

FIGURE 6
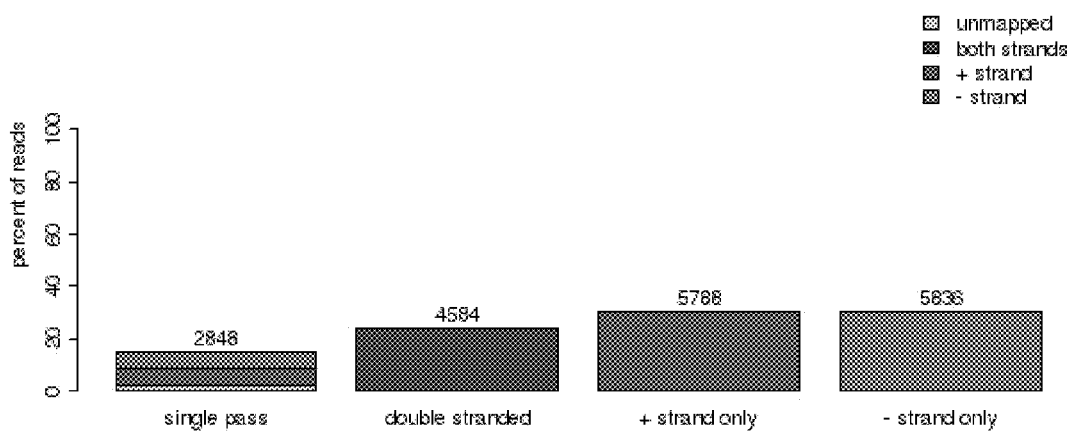
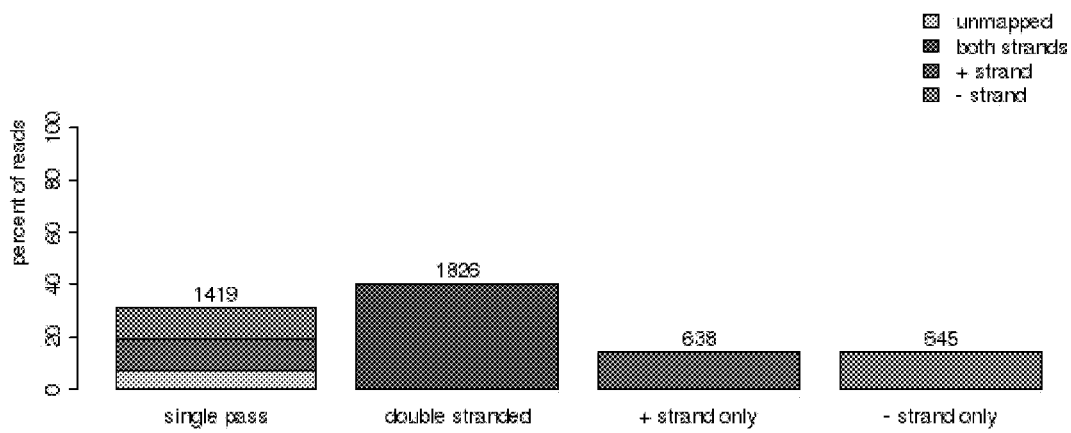
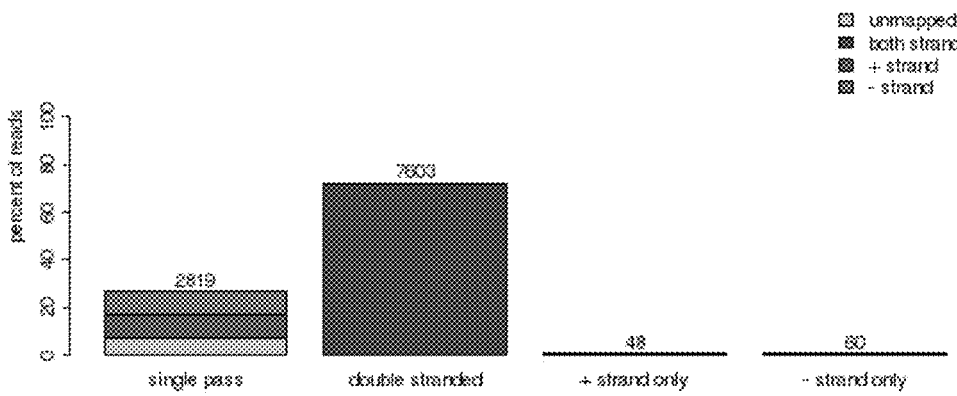

FIGURE 7
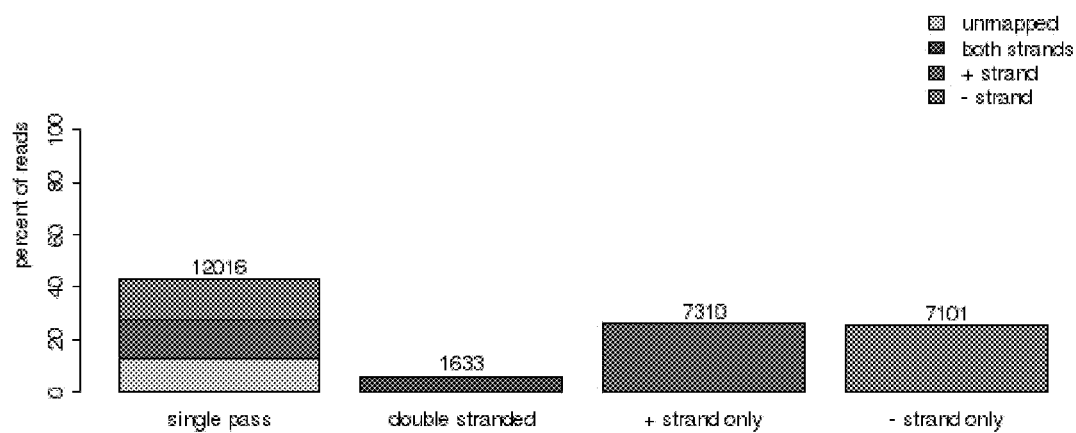
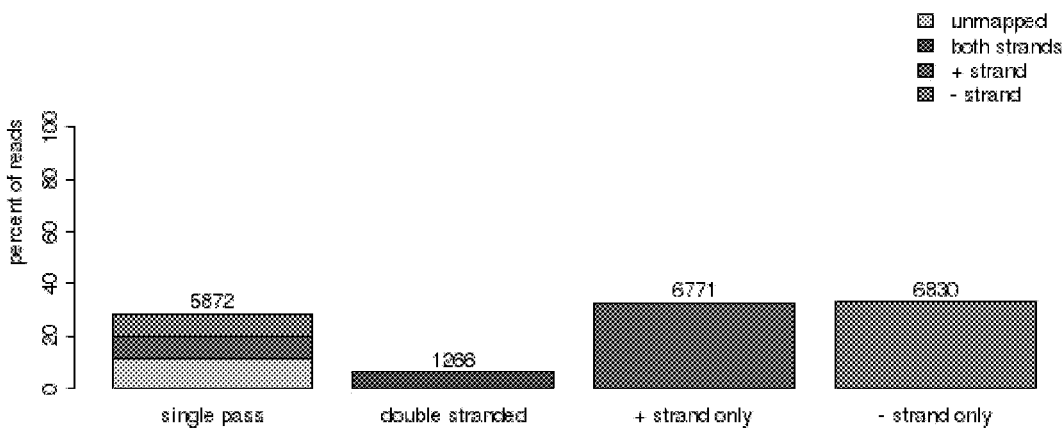

FIGURE 8
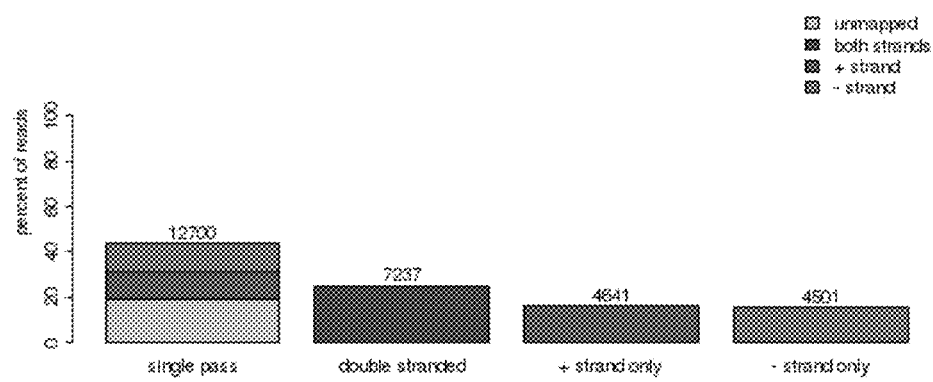
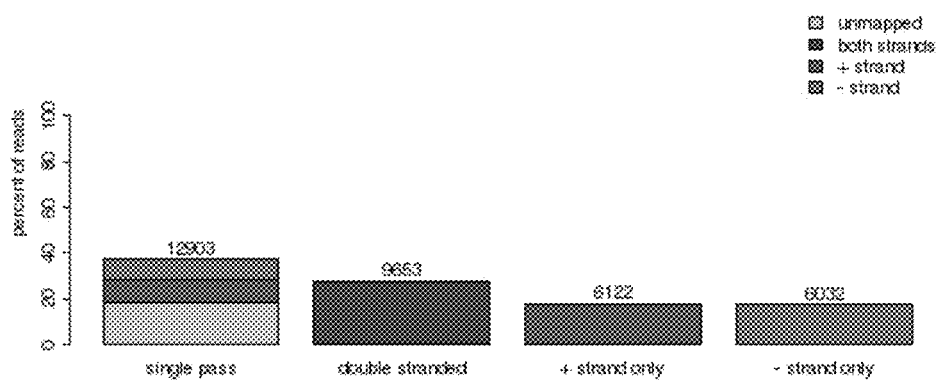
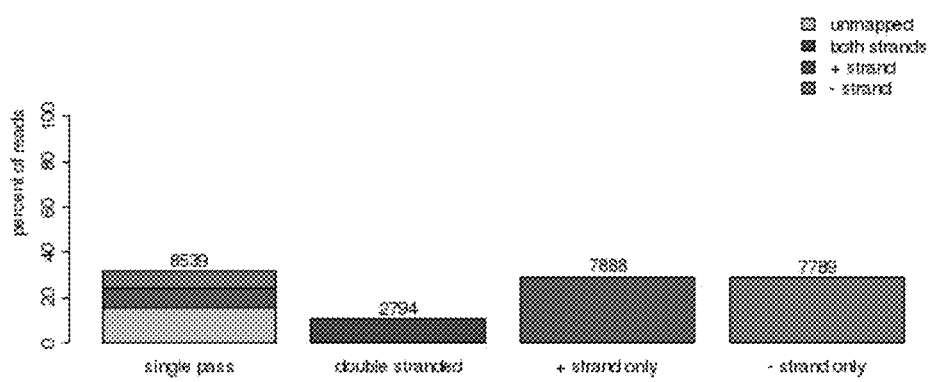

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded sequence

<400> SEQUENCE: 1
aacggaggag gaggaaaag                                                    19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded sequence

<400> SEQUENCE: 2
gttgttgttg agagagatt                                                19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded sequence

<400> SEQUENCE: 3
gttgttgttg agagagatt                                                19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded sequence

<400> SEQUENCE: 4
aacggaggag gaggaaaag                                                19

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded sequence

<400> SEQUENCE: 5
ctcctccgtt tttgagagag att                                           23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded sequence

<400> SEQUENCE: 6
atctctctct acgactgtcc tc                                            22

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded sequence

<400> SEQUENCE: 7
gtcctcctcc tccgtttttt gagagagatt                                    30

```
-continued

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Single stranded sequence

<400> SEQUENCE: 8
atctctctct actgactg                                                   18
```

GENERATION OF SINGLE-STRANDED CIRCULAR DNA TEMPLATES FOR SINGLE MOLECULE SEQUENCING

SEQUENCE LISTING

The instant application contains a Sequence Listing which has been submitted electronically in ASCII format and is hereby incorporated by reference in its entirety. Said ASCII copy, created on Jan. 7, 2021, is named 34422-US1_SL.txt and is 2,602 bytes in size.

FIELD OF THE INVENTION

The invention relates to the field of nucleic acid analysis and more specifically, to preparing templates for nucleic acid sequencing.

BACKGROUND OF THE INVENTION

Single molecule nucleic acid sequencing including nanopore sequencing generally requires consensus building due to the high error rate of the technology. There are library preparation methods that produce circular double stranded templates that allow the target sequence to be read multiple times in a single long polymerase read. See U.S. Pat. Nos. 7,302,146 and 8,153,375. Linear nucleic acids can be converted into a circular form for amplification and subsequent detection and quantification, see U.S. Pat. No. RE44265. When sequenced on a platform using the Single Molecule Real Time (SMRT) technology (Pacific Biosciences, Menlo Park, Cal.) the polymerase reads the library molecule producing a contiguous read (polymerase read) consisting of alternating sense and antisense copies of the library molecules. There may be instances where due to technical application or other constraints, only one of the DNA strands of an original double stranded molecule is read. The invention is a method to produce and sequence a circular library containing only single strands of the target sequence. The method has multiple advantages described in detail below.

SUMMARY OF THE INVENTION

In one embodiment, the invention is a method of separately sequencing each strand of a double stranded target nucleic acid comprising the steps of: in a reaction mixture, joining a double stranded target nucleic acid to an adaptor to form an adapted target nucleic acid wherein the adaptor comprises primer binding sites; amplifying the adapted target nucleic acid with a pair of primers complementary to the primer binding sites thereby forming an amplicon, wherein one primer in the pair of primers comprises a modified nucleotide affecting a rate of digestion by an exonuclease; contacting the reaction mixture with an exonuclease thereby eliminating from the reaction mixture the first of the two complementary strands of the amplicon; circularizing the second of the two complementary strands of the amplicon to form a single stranded circle; annealing a sequencing primer to the single stranded circle; and extending the primer thereby sequencing one strand of the target nucleic acid. The adaptor may be joined by ligation, e.g., by joining of cohesive ends of the target nucleic acid and the adaptor. The adaptor may comprise a double stranded part and a single stranded part comprising two non-annealed portions, at least one barcode and at least one primer binding site that can be located on same or separate arms of the adaptor. The sequencing primer binding site may also be in the adaptor. The modified nucleotide may be a 5'-phoshorylated terminal nucleotide with Lambda exonuclease. The modified nucleotide may comprise a phosphorothioate group with T5 or T7 exonuclease. The method may further comprise a second exonuclease digestion step after the circularization step. The second exonuclease may be a combination of double-strand specific exonuclease and a single-strand specific exonuclease, e.g., Exonuclease I, Exonuclease III, T5 exonuclease and Exonuclease VII.

The circularization may occur by ligation, such as splint ligation or single-strand ligation. The method may further comprise a target enrichment step, e.g., by capture via target-specific probes bound to solid support. The method may further comprise contacting the reaction mixture with a DNA damage-specific agent selected from glycosylase and endonuclease.

In some embodiments, the invention is a method of making a library of single stranded nucleic acids from double stranded target nucleic acids in a sample, the method comprising the steps of: in a reaction mixture, joining double stranded target nucleic acids to adaptors to form adapted target nucleic acids wherein adaptors comprise primer binding sites; amplifying the adapted target nucleic acids with a pair of primers complementary to the primer binding sites thereby forming amplicons, wherein one primer in the pair of primers comprises a modified nucleotide affecting a rate of digestion by an exonuclease; contacting the reaction mixture with an exonuclease thereby eliminating from the reaction mixture the first of the two complementary strands of the amplicons; circularizing the second of the two complementary strands of the amplicons to form single stranded circles thereby forming a library of single stranded circular target nucleic acids.

In some embodiments, the invention is a method of determining the sequence of a library of target nucleic acid in a sample, the method comprising the steps oft forming a library of single stranded circular target nucleic acids outlined above; annealing a primer to the primer binding site in each single stranded circle; extending the primer thereby sequencing the library.

In some embodiments, the invention is a method of separately sequencing each strand of a double stranded target nucleic acid comprising the steps of in a reaction mixture, amplifying a target nucleic acid with a pair of target-specific primers thereby forming an amplicon, wherein one primer in the pair of primers comprises a modified nucleotide inhibiting digestion by an exonuclease; contacting the reaction mixture with an exonuclease thereby eliminating from the reaction mixture the first of the two complementary strands of the amplicon; circularizing the second of the two complementary strands of the amplicon to form a single stranded circle; annealing a sequencing primer to the single stranded circle; extending the primer thereby sequencing one strand of the target nucleic acid.

In some embodiments, the invention is a method of making a library of single stranded nucleic acids from double stranded target nucleic acids in a sample, the method comprising the steps of; in a reaction mixture, amplifying target nucleic acids with a pair of target-specific primers thereby forming amplicons, wherein one primer in the pair of primers comprises a modified nucleotide affecting a rate of digestion by an exonuclease; contacting the reaction mixture with an exonuclease thereby eliminating from the reaction mixture the first of the two complementary strands of the amplicons; circularizing the second of the two complementary strands of the amplicons to form single stranded circles thereby forming a library of single stranded circular target nucleic acids.

In some embodiments, the invention is a method of determining the sequence of a library of target nucleic acid in a sample, the method comprising the steps of: forming a library of single stranded circular target nucleic acids by the method outlined above; annealing a primer to the primer binding site in each single stranded circle; extending the primer thereby sequencing one strand of each target nucleic acid in the library.

In some embodiments, the invention is a method of separately sequencing each strand of a double stranded target nucleic acid comprising the steps of: in a reaction mixture, joining a double stranded target nucleic acid to an adaptor to form an adapted target nucleic acid wherein the adaptor comprises primer binding sites; amplifying the adapted target nucleic acid with a pair of primers complementary to the primer binding sites thereby forming an amplicon, wherein one primer in the pair of primers comprises a ligand for a capture moiety; separating the two strands of the amplicon; contacting the reaction mixture with the capture moiety thereby capturing the first of the two strands of the amplicon; circularizing the strands of the amplicon to form a single stranded circle; annealing a sequencing primer to the single stranded circle; extending the primer thereby sequencing one strand of the target nucleic acid. The method may further comprise the use of a strand separation enhancer selected from single-strand binding (SSB) protein, $C_0t$ DNA, alkali, glycerol, urea, DMSO and formamide. The captured single strand may be retained and the free single strand may be eliminated. Or the captured single strand may be eliminated and the free single strand may be retained.

In some embodiments, the invention is a method of making a library of single stranded nucleic acids from double stranded target nucleic acids in a sample, the method comprising the steps of: in a reaction mixture, joining double stranded target nucleic acids to an adaptor to form adapted target nucleic acids, wherein the adaptor comprises primer binding sites; amplifying the adapted target nucleic acids with a pair of primers complementary to the primer binding sites thereby forming amplicons, wherein one primer in the pair of primers comprises a ligand for a capture moiety; separating the two strands of the amplicons; contacting the reaction mixture with the capture moiety thereby capturing the first of the two complementary strands of the amplicon; circularizing the complementary strands of the amplicon to form single stranded circles thereby forming a library of single stranded circular target nucleic acids.

In some embodiments, the invention is a method of determining the sequence of a library of target nucleic acid in a sample, the method comprising the steps of: forming a library of single stranded circular target nucleic acids by the method outlines above; annealing a primer to the primer binding site in each single stranded circle; extending the primer thereby sequencing one strand of each target nucleic acid in the library.

In some embodiments, the invention is a method of preferentially sequencing one strand of a double stranded target nucleic acid comprising the steps of: in a reaction mixture, joining a double stranded target nucleic acid to an adaptor to form an adapted target nucleic acid wherein the adaptor comprises primer binding sites; amplifying the adapted target nucleic acid with a pair of primers complementary to the primer binding sites, the pair comprising a limiting amount of a limiting primer and an excess amount of an excess primer; circularizing the extension products to form single stranded circles; annealing a sequencing primer to the single stranded circles; extending the primer thereby preferentially sequencing one strand of the target nucleic acid. The excess primer may comprise a modified nucleotide affecting a rate of digestion by an exonuclease and further comprising contacting the reaction mixture with an exonuclease thereby eliminating from the reaction mixture the extension product of the limiting primer. In some embodiments, the excess primer may comprise a ligand for an affinity capture moiety to capture and retain the extension product of the excess primer. In some embodiments, the limiting primer may comprise a ligand for an affinity capture moiety to capture and remove the extension product of the limiting primer.

BRIEF DESCRIPTION OF THE DRAWINGS

FIG. 4 shows the result of sequencing the control libraries.

FIG. 5 shows the result of sequencing the libraries made using Method 1.

FIG. 6 shows the result of sequencing the libraries made using Method 1 with a nanopore adaptor.

FIG. 7 shows the result of sequencing the libraries made using Method 2 with T7 exonuclease.

FIG. 8 shows the result of sequencing the libraries made using Method 2 with Lambda exonuclease.

DETAILED DESCRIPTION OF THE INVENTION

Definitions

Figure 1:
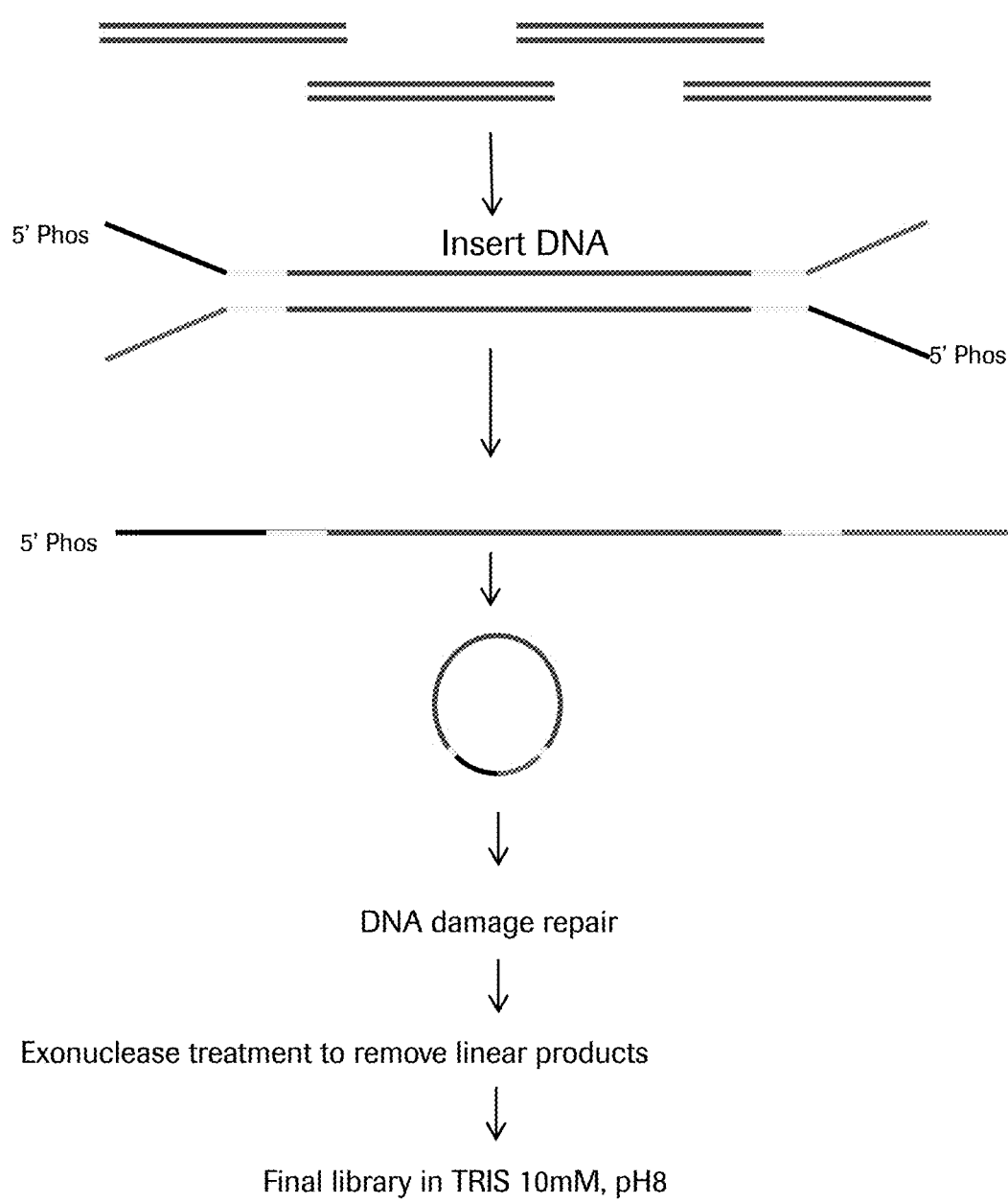
FIG. 1 shows a workflow of the first embodiment of the method of making a library of circular single stranded nucleic acids (Method 1).

The following definitions aid in understanding of this disclosure.

The term "sample" refers to any composition containing or presumed to contain target nucleic acid. This includes a sample of tissue or fluid isolated from an individual for example, skin, plasma, serum, spinal fluid, lymph fluid, synovial urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (ctDNA) or circulating tumor DNA (ctDNA).

The term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double-stranded and will generally contain phosphodiester bonds, although in some cases, nucleotide analogs may have other linkages. Nucleic acids may include naturally occurring bases (adenosine, guanosine, cytosine, uracil and thymidine) as well as non-natural bases. Some examples of non-natural bases include those described in, e.g., Seela et al., (1999) *Helv. Chim. Acta* 82:1640. The non-natural bases may have a particular function, e.g., increasing the stability of the nucleic acid duplex, inhibiting nuclease digestion or blocking primer extension or strand polymerization.

The terms "polynucleotide" and "oligonucleotide" are used interchangeably. Polynucleotide is a single-stranded or a double-stranded nucleic acid. Oligonucleotide is a term sometimes used to describe a shorter polynucleotide. Oligonucleotides are prepared by any suitable method known in the art, for example, by a method involving direct chemical synthesis as described in Narang et al. (1979) *Meth. Enzymol.* 68:90-99; Brown et al. (1979) *Meth. Enzymol.* 68:109-151; Beaucage et al. (1931) *Tetrahedron Lett.* 22:1859-1862; Matteucci et al. (1981) *J. Am. Chem. Soc.* 103:3185-3191.

The term "primer" refers to a single-stranded oligonucleotide which hybridizes with a sequence in the target nucleic acid ("primer binding site") and is capable of acting as a point of initiation of synthesis along a complementary strand of nucleic acid under conditions suitable for such synthesis.

The term "adaptor" means a nucleotide sequence that may be added to another sequence so as to import additional properties to that sequence. An adaptor is typically an oligonucleotide that can be single- or double-stranded, or may have both a single-stranded portion and a double-stranded portion.

The term "ligation" refers to a condensation reaction joining two nucleic acid strands wherein a 5'-phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double-stranded molecule thus joining two double-stranded molecules. Ligation may also join two ends of a strand within a double-stranded molecule thus repairing a nick in the double-stranded molecule.

The term "barcode" refers to a nucleic acid sequence that can be detected and identified Barcodes can be incorporated into various nucleic acids. Barcodes are sufficiently long e.g., 2, 5, 20 nucleotides, so that in a sample, the nucleic acids incorporating the barcodes can be distinguished or grouped according to the barcodes.

The term "multiplex identifier" or "MID" refers to a barcode that identifies a source of a target nucleic acids (e.g., a sample from which the nucleic acid is derived). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated.

The term "unique molecular identifier" or "UID" refers to a barcode that identities a nucleic acid to which it is attached. All or substantially all the target nucleic acids from the same sample will have different UIDs. All or substantially all of the progeny (e.g., amplicons) derived from the same original target nucleic acid will share the same UID.

The term "universal primer" and "universal priming binding site" or "universal priming site" refer to a primer and primer binding site present in (typically, through in vitro addition to) different target nucleic acids. The universal priming site is added to the plurality of target nucleic acids using adaptors or using target-specific (non-universal) primers having the universal priming site in the 5"-portion. The universal primer can bind to and direct primer extension from the universal priming site.

More generally, the term "universal" refers to a nucleic acid molecule (e.g., primer or other oligonucleotide) that can be added to any target nucleic acid and perform its function irrespectively of the target nucleic acid sequence. The universal molecule may perform its function by hybridizing to the complement, e.g., a universal primer to a universal primer binding site or a universal circularization oligonucleotide to a universal primer sequence.

As used herein, the terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "amplification" refers to a process of making additional copies of the target nucleic acid. Amplification can have more than one cycle, e.g., multiple cycles of exponential amplification. Amplification may have only one cycle (making a single copy of the target nucleic acid). The copy may have additional sequences, e.g., those present in the primers used for amplification. Amplification may also produce copies of only one strand (linear amplification) or preferentially one strand (asymmetric PCR).

The term "sequencing" refers to any method of determining the sequence of nucleotides in the target nucleic acid.

Single molecule sequencing typically involves building consensus sequence from multiple reads in part to mitigate the high error rate of the technology. In some methods consensus is built from multiple readings of the same template molecule, in particular, a circular molecule. Sequencing library preparation methods convert the library of target molecules into a library of circular templates. One such method uses hairpin adapters attached at either end of a double stranded target molecule. Sec U.S. Pat. Nos. 7,302,146 and 8,153,375. During sequencing, the polymerase reads the library molecule continuously producing a contiguous read consisting of alternating sense and antisense copies of the library molecule interspersed with adapter sequences. After the polymerase read in split into sub reads, the subreads are used to produce a high accuracy consensus sequence, termed circular consensus sequence. In some applications, it may be desirable to read each strand of a double stranded molecule separately. This invention is a method to produce and sequence a library consisting of single stranded circles each containing a library insert.

The present invention comprises detecting a target nucleic acid in a sample. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, and/or fecal samples), The sample may comprise whole blood or blood fractions where tumor cells may be present. In some embodiments, the sample, especially a liquid sample may comprise cell-free material such as cell-free DNA or RNA including cell-free tumor DNA or tumor RNA. The present invention is especially suitable for analyzing rare and low quantity targets. In some embodiments, the sample is a cell free sample, e.g., cell-free blood-derived sample where cell-free tumor DNA or tumor RNA are present. In other embodiments, the sample is a cultured sample, e.g., a culture or culture supernatant containing or suspected to contain an infectious agent or nucleic acids derived from the infectious agent. In some embodiments, the infectious agent is a bacterium, a protozoan, a virus or a *mycoplasma*.

A target nucleic acid is the nucleic acid of interest that may be present in the sample. In some embodiments, the target nucleic acid is a gene or a gene fragment. In other embodiments, the target nucleic acid contains a genetic variant, e.g., a polymorphism, including a single nucleotide polymorphism or variant (SNP or SNV), or a genetic rearrangement resulting e.g., in a gene fusion. In some embodiments, the target nucleic acid comprises a biomarker. In other embodiments, the target nucleic acid is characteristic of a particular organism, e.g., aids in identification of the pathogenic organism or a characteristic of the pathogenic organism, e.g., drug sensitivity or drug resistance. In yet other embodiments, the target nucleic acid is characteristic of a human subject, e.g., the HLA or KIR sequence defining the subject's unique HLA or KIR genotype. In yet other embodiments, all the sequences in the sample are target nucleic acids e.g., in shotgun genomic sequencing.

In an embodiment of the invention, a double-stranded target nucleic acid is converted into the template configuration of the invention. In some embodiments, the target nucleic acid occurs in nature in a single-stranded form (e.g., RNA, including mRNA, microRNA, viral RNA; or single-stranded viral DNA). The single-stranded target nucleic acid is converted into double-stranded form to enable the further steps of the claimed method.

Longer target nucleic acids may be fragmented although in some applications longer target nucleic acids may be desired to achieve a longer read. In some embodiments, the target nucleic acid is naturally fragmented, e.g., circulating cell-free DNA (cfDNA) or chemically degraded DNA such as the one founds in preserved samples. In other embodiments, the target nucleic acid is fragmented in vitro, e.g., by physical means such as sonication, or by endonuclease digestion, e.g., restriction digestion.

In some embodiments, the invention comprises a target enrichment step. The enrichment may be by capturing the target sequences via one or more targets-specific probes. The nucleic acids in the sample may be denatured and contacted with single-stranded target-specific probes. The probes may comprise a ligand for an affinity capture moiety so that after hybridization complexes are formed, they are captured by providing the affinity capture moiety. In some embodiments, the affinity capture moiety is avidin or streptavidin and the ligand is biotin. In some embodiments, the moiety is bound to solid support. As described in further detail below, the solid support may comprise superparamagnetic spherical polymer particles such as DYNABEADS™ magnetic beads or magnetic glass particles.

In some embodiments of the present invention, adaptor molecules are ligated to the target nucleic acid. The ligation can be a blunt-end ligation or a more efficient cohesive-end ligation. The target nucleic acid or the adaptors may be rendered blunt-ended by "end repair" comprising strand-filling, i.e., extending a 3'-terminus by a DNA polymerase to eliminate a 5'-overhang. In some embodiments, the blunt-ended adaptors and target nucleic acid may be rendered cohesive by addition of a single nucleotide to the 3'-end of the adaptor and a single complementary nucleotide to the 3'-ends of the target nucleic acid, e.g., by a DNA polymerase or a terminal transferase. In yet other embodiments, the adaptors and the target nucleic acid may acquire cohesive ends (overhangs) by digestion with restriction endonucleases. The latter option is more advantageous for known target sequences that are known to contain the restriction enzyme recognition site. In some embodiments, other enzymatic steps may be required to accomplish the ligation. In some embodiments, a polynucleotide kinase may be used to add 5'-phosphates to the target nucleic acid molecules and adaptor molecules.

Figure 3:
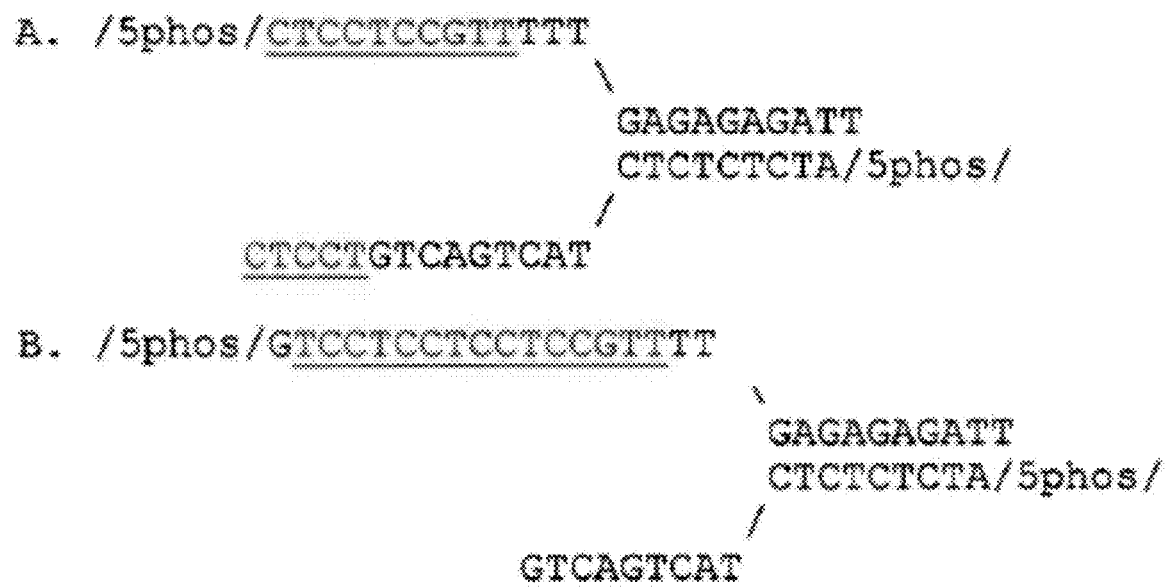
FIG. 3 is a diagram of the Y-shaped adaptor. (A) shows an adaptor with portions of the primer binding site (underlined) split between the arms of the adaptor. (B) shows an adaptor with the entire primer binding site (underlined) present in one arm of the adaptor. The sequences correspond to SEQ ID NO. 5-8

In embodiments where adaptors are added independently of the sequence of the target nucleic acid, for example, by ligation the target nucleic acids in the sample receive the same adaptor molecule at each end. To distinguish the strands of the resulting adapted target nucleic acid, the adaptor may have a Y structure, see e.g., U.S. Pat. Nos. 8,053,192, 8,182,989 and 8,822,150. (FIG. 3)

In some embodiments, adaptors comprise a primer binding site, e.g., an amplification primer binding site or a sequencing primer binding site. The primer binding site may be contiguous on an adaptor, FIG. 3, panel (B). In some embodiments, to increase specificity of sequencing (i.e., only circularized molecules are sequenced), the sequencing primer binding site may be discontinuous on the adaptor arms as shown in FIG. 3, panel (A) so that the functional primer binding site is formed only upon circularization of the adapted target nucleic acid when the arms of the adaptor are joined together in the circular molecule.

In some embodiments, the adaptor molecules are in vitro synthesized artificial sequences. In other embodiments, the adaptor molecules are in vitro synthesized naturally-occurring sequences. In yet other embodiments, the adaptor molecules are isolated naturally occurring molecules.

In some embodiments, the invention is a method comprising a step of amplifying the target nucleic acid. The amplification may be by exponential polymerase chain reaction (PCR), linear amplification of only one strand or any other method that utilizes oligonucleotide primers. Various PCR conditions are described in PCR Strategies (M. A. Innis, D. H. Gelfand, and J. J. Sninsky eds., 1995, Academic Press, San Diego, CA) at Chapter 14; *PCR Protocols: A Guide to Methods and Applications* (M. A, Innis, D. H. Gelfand, J. J. Sninsky, and T. J. White eds., Academic Press, NY, 1990).

In some embodiments, amplification utilizes a universal primer binding site present in the adaptor that is conjugated to the target sequence as set forth above. In other embodiments, a gene-specific (target-specific) primer or primer pair is used. In some embodiments, primers contain a 5'-overhang comprising adaptor sequences, e.g., barcodes or sequencing primer binding sites. The use of such primers dispenses with the adaptor ligation step in the method of the instant invention.

In some embodiments, amplification involves asymmetric PCR that generates excess of one of the two strands as descried e.g., in Gyllensten U. B. and Erlich H. A. (1983) *Generation of single-stranded DNA by the polymerase chain reaction and its application to direct sequencing of the HLA-DQA locus, PNAS*, 85:7652. In that embodiment, a pair of primers consists of an excess primer present in excess amount and a limiting primer present in limiting amount. The resulting amplification preferentially comprises the strand representing extension product of the excess primer. Lithe method of the invention includes a step of asymmetric PCR, the resulting single stranded circles would preferentially comprise one strand which is the extension product of the excess primer. To further enrich the reaction for one strand, the step of exonuclease digestion as described herein may be employed. Specifically, the excess primer may comprise an exonuclease resistant modification so that prior to circularization, the extension product of the limiting primer could be eliminated via exonuclease digestion. Alternatively, the excess primer may comprise a ligand for the affinity capture moiety so that the extension product of the excess primer could be captured using the affinity capture moiety and retained for further analysis. Yet in another alternative, the limiting primer may comprise a ligand for the affinity capture moiety so that the extension product of the limiting primer could be captured using the affinity capture moiety and discarded while the product of the excess primer is retained in the reaction mixture for further analysis.

In some embodiments, the invention comprises introduction of barcodes into the target nucleic acids. Sequencing individual molecules typically requires molecular barcodes such as described e.g., in U.S. Pat. Nos. 7,393,665, 8,168,385, 8,481,292, 8,685,678, and 9,722,368. A unique molecular barcode is a short artificial sequence added to each molecule in a sample such as a patient's sample typically during the earliest steps of in vitro manipulations. The barcode marks the molecule and its progeny. The unique molecular barcode (UID) has multiple uses. Barcodes allow tracking each individual nucleic acid molecule in the sample to assess, e.g., the presence and amount of circulating tumor DNA (ctDNA) molecules in a patient's blood in order to detect and monitor cancer without a biopsy. Sec U.S. patent application Ser. Nos. 14/209,807 and 14/774,518. Unique molecular barcodes can also be used for sequencing error correction. The entire progeny of a single target molecule is marked with the same barcode and forms a barcoded family. A variation in the sequence not shared by all members of the barcoded family is discarded as an artifact and not a true mutation. Barcodes can also be used for positional deduplication and target quantification, as the entire family represents a single molecule in the original sample. See Id.

In some embodiments of the present invention, adaptors comprise one or more barcodes. A barcode can be a multiplex sample ID (MID) used to identify the source of the sample where samples are mixed (multiplexed). The barcode may also serve as a UID used to identify each original molecule and its progeny. The barcode may also be a combination of a UID and an MID. In some embodiments, a single barcode is used as both UID and MID.

In some embodiments, each barcode comprises a predefined sequence. In other embodiments, the barcode comprises a random sequence. Barcodes can be 1-20 nucleotides long.

In some embodiments, the method further comprises a step of separating the strands of the adapted target nucleic acid. In some embodiments, both of the separated strands are retained for downstream analysis, e.g., sequencing. The two strands may be separated by physical means, i.e., alkaline denaturation or heat denaturation.

In some embodiments, the strands are separated enzymatically e.g., by selective degradation of one strand by a nuclease. In some embodiments, the exonuclease has a 5'->3' activity. Advantageously, only one strand may be made susceptible to exonuclease digestion while the second strand is protected from exonucleases, either property being conferred by modified nucleotides present in the strand. In some embodiments the modified nucleotide is a 5'-phosphorylated terminal nucleotide and the exonuclease is Lambda exonuclease digesting the 5% phoshorylated strand while the non-phosphorylated strand is retained for subsequent steps. In other embodiments, the modified nucleotide comprises a phosphorothioate group and the exonuclease is selected from T5 and T7 exonuclease digesting the unmodified strand while the modified strand is retained for subsequent steps.

In other embodiments, one strand is marked for retention via affinity capture. For example, one of the amplification primers may comprise an affinity ligand (e.g., biotin) that will enable the strand to be captured by an affinity capture moiety (e.g., via streptavidin) and retained while the complementary strand may be discarded. In some embodiments, the affinity capture utilizes the affinity molecule (e.g., streptavidin) bound to solid support. The solid support may be capable of suspension in a solution (e.g., a glass bead, a magnetic bead, a polymer bead or another like particle), or a solid-phase support (e.g., a silicon wafer, a glass slide, or the like). Examples of solution-phase supports include superparamagnetic spherical polymer particles such as DYNABEADS™ magnetic beads or magnetic glass particles such as described in U.S. Pat. Nos. 656,568, 6,274,386, 7,371,330, 6,870,047, 6,255,477, 6,746,374 and 6,253,531.

In some embodiments, strand separation is enhanced by various agents selected from the single-strand binding protein, e.g., bacterial SSB, low complexity DNA $C_0t$ DNA (DNA enriched for repetitive sequences), or chemical agents such as alkali, glycerol, urea, DMSO or formamide.

The method further comprises a step of circularizing a single stranded nucleic acid. The ligation step utilizes a ligase capable of catalyzing a reaction between a 5'-phosphate and a 3'-OH group of a nucleic acid. In some embodiments, the ligase is a DNA or RNA ligase capable of template-independent ligation such as a viral ligase described e.g., in Pub. No. WO2010094040. Further, a non-enzymatic reagent can be used to form the phosphordiester bond between the 5'-phosphate of the primer extension product and the 3'-OH of the adaptor as described e.g., in US20140193860. In some embodiments, the ligase is a thermostable single stranded RNA or DNA ligase such as the Thermophage Ligase or its derivatives such as Circligase™ and Circligase™ II (Epicentre Tech., Madison, Wisc.). In some embodiments, a splint is used to enable a double-strand ligase, e.g., T4 ligase activity. A splint oligonucleotide is complementary to both strands of the adaptor arranged head-to-tail.

In some embodiments, the invention comprises an exonuclease digestion step that eliminates linear (non-circular) nucleic acids from the reaction mixture and enriches for circular nucleic acids. The linear nucleic acids may comprise uncircularized target nucleic acid strands, unused primers and adaptors.

In some embodiments, the exonuclease is a single strand-specific exonuclease, a double strand-specific exonuclease or a combination thereof. In some embodiments, the exonuclease has a 3'->5' activity. The exonuclease may be one or more of Exonuclease I, Exonuclease III and Exonuclease VII.

In some embodiments, the invention is a method of making a library of sequencing-ready circular single stranded target nucleic acids as described herein and the library produced by the method. Specifically, the library comprises a collection of circular single strands derived from nucleic acids present in a sample. The single stranded circular molecules of the library comprise target sequences joined with adaptor sequences.

In some embodiments, the present invention comprises detecting target nucleic acids in a sample by nucleic acid sequencing. Multiple nucleic acids, including all the nucleic acids in a sample may be converted into the template configuration of the invention and sequenced. In some embodiments, the library of single stranded circular molecules can be subjected to nucleic acid sequencing.

In some embodiments, the method further comprises a step of eliminating damaged or degraded targets in order to improve the quality and length of sequencing reads. The step may comprise contacting the reaction mixture with one or more of uracil DNA N-glycosylase (UNG or UDG), AP nuclease and Fpg (formamidopyrimidine [fapy]-DNA glycosylase), also known as 8-oxoguanine DNA glycosylase in order to degrade such damaged target nucleic acids.

As described above, the adaptor or the target-specific primer may comprise a sequencing primer binding site which can initiate a sequencing read of each strand.

Sequencing can be performed by any method known in the art. Especially advantageous is the high-throughput single molecule sequencing capable of reading circular target nucleic acids. Examples of such technologies include the Pacific BioSciences platform utilizing the SMRT (Pacific Biosciences, Menlo Park, Cal.) or a platform utilizing nanopore technology such as those manufactured by Oxford Nanopore Technologies (Oxford, UK) or Roche Sequencing Solutions (Roche Genia, Santa Clara, Cal.) and any other presently existing or future DNA sequencing technology that does or does not involve sequencing by synthesis. The sequencing step may utilize platform-specific sequencing primers. Binding sites for these primers may be introduced in the method of the invention as described herein, i.e., by being a part of second adaptors or amplification primers.

Analysis and Error Correction

In some embodiments, the sequencing step involves sequence analysis including a step of sequence aligning. In some embodiments, aligning is used to determine a consensus sequence from a plurality of sequences, e.g., a plurality having the same barcodes (UID). In some embodiments barcodes (UIDs) are used to determine a consensus from a plurality of sequences all having an identical barcode (UID). In other embodiments, barcodes (UIDs) are used to eliminate artifacts, i.e., variations existing in some but not all sequences having an identical barcode (UID). Such artifacts resulting from PCR errors or sequencing errors can be eliminated.

In some embodiments, the number of each sequence in the sample can be quantified by quantifying relative numbers of sequences with each barcode (UID) in the sample. Each UID represents a single molecule in the original sample and counting different UIDs associated with each sequence variant can determine the fraction of each sequence in the original sample. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

As is shown in FIG. 1, one embodiment of the method involves ligating an adaptor, such as a V-shaped adaptor to a target molecule or a library of target molecules. The adaptor may contain barcodes such as sample ID (SID) or unique molecular ID (UID) and a sequencing primer binding site. Further, the 5'-end of the adaptor molecule is phosphorylated to enable a ligation step. In the next step, the strands are separated and maintained in single-stranded form either by physical (temperature) or chemical (alkaline) means. Single-stranded state may be further enhanced by presence of single strand stabilizing gents such as the single-strand binding protein, e.g., bacterial SSB. The strands may also be separated by removing one strand with an exonuclease. In the next step, the single strands are self-ligated (circularized) with the help of a single-strand ligase or a like reagent capable of linking the 5'-phosphate and a 3'-OH of the single strands. In some embodiments, a splint is used to enable a double-strand ligase, e.g., T4 ligase activity. Undesirable byproducts such as linear concatemers, excess adaptors or unobligated target nucleic acids are removed e.g., by exonuclease digestion to which they are susceptible by virtue of having free 5'- and 3'-ends. A combination of Exonuclease VII and Exonuclease III may be used. The resulting circular single-stranded target nucleic acid or a library of circular single-stranded target nucleic acids is sequenced by annealing a sequencing primer to a primer binding site in the adaptor sequence.

Figure 2:
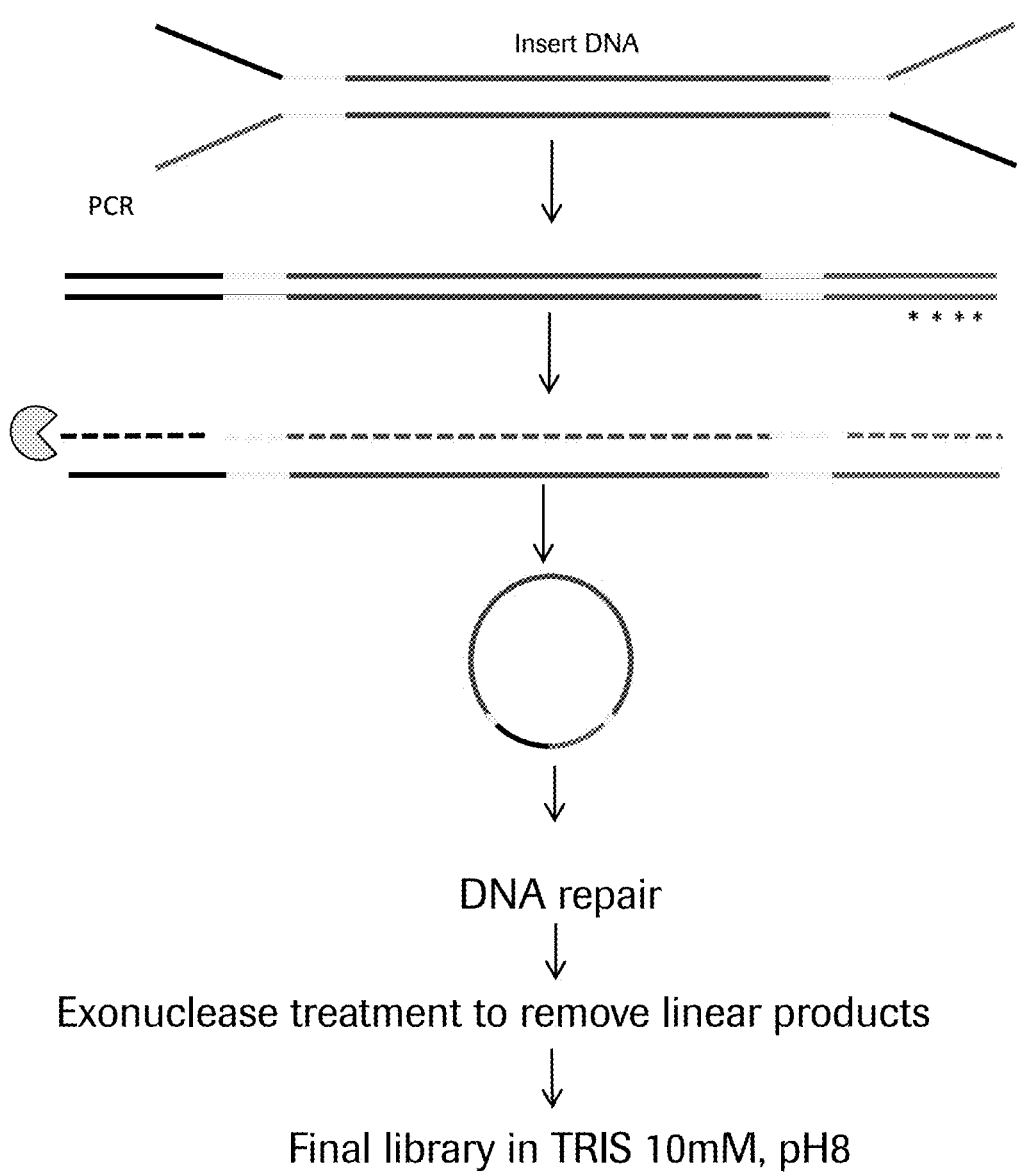
FIG. 2 shows a workflow of the second embodiment of the method of making a library of circular single stranded nucleic acids including a PCR step (Method 2).

As is shown in FIG. 2, one embodiment of the method involves ligating an adaptor, such as a Y-shaped adaptor to a target molecule or a library of target molecules. The adaptor may contain barcodes such as sample ID (SID) or unique molecular ID (UID) and a primer binding site. In the next step, the ligated adapted target molecule or a library of adapted target molecules is amplified using universal primers complementary to the primer binding site. The primers comprise a phosphorylated 5'-end to enable a ligation step. In the next step, the strands are separated and maintained in single-stranded form either by physical (temperature) or chemical (alkaline) means. Single-stranded state may be further enhanced by presence of single strand stabilizing gents such as the single-strand binding protein, e.g., bacterial SSB. The strands may also be separated by removing one strand with an exonuclease. One of the primers may comprise a modification preventing exonuclease digestion of the primer and the primer extension product (i.e., amplicon strand). One of the primers may alternatively, comprise a modification enabling exonuclease digestion of the primer and amplicon strand. In the next step, the remaining single strands are self-ligated (circularized) with the help of a single-strand ligase or a like reagent capable of linking the 5'-phosphate and a 3'-OH of the single strands or with the double-strand ligase aided by a splint oligonucleotide. Undesirable byproducts such as linear concatemers, excess adaptors or target nucleic acids lacking adaptors are removed e.g., by exonuclease digestion to which they are susceptible by virtue of having free 3'- and 3'-ends. The resulting circular single-stranded target nucleic acid or a library of circular single-stranded target nucleic acids is sequenced by annealing a sequencing primer to a primer binding site in the adaptor sequence.

EXAMPLES

Example 1. Preparing and Sequencing a Circular Single Stranded Unamplified Library Sequencing libraries were prepared according to the method shown in FIG. 1 from 500 ng or 1 ug of E. coli genomic DNA. The library included the adaptor specific for the Pacific BioSciences RSII sequencing platform. The exonuclease resistant (likely circular) material was resolved using a Bioanalyzer RNA pico assay. Final library yield was 10-20% of the starting DNA mass.

The resulting libraries were sequenced on Pacific BioSciences RSII platform (Pacific BioSciences, Menlo Park, Cal.) The results are shown on FIG. 4 and FIG. 5.

In addition to the single stranded circular libraries according to FIG. 1, two types of controls were prepared: 1) a conventional double stranded library prepared using hairpin adaptors; and 2) a library prepared by the method of FIG. 1 but skipping the denaturation step thereby re-forming the double-stranded circular templates similar to control 1. All libraries were sequenced on the Pacific Biosciences RSII platform. As expected, the controls comprised ~80% of double stranded DNA and less than 1% single stranded DNA (FIG. 4), while ~40% of the library prepared according to the method of the invention comprised only one strand. (FIG. 5).

The experiment was repeated with the library including an adaptor specific for a nanopore-based sequencing platform (Roche Genia). The library was sequenced on RSII indicating that 30% (with SSB) and 61% (without SSB) was single stranded. The control libraries contained <1% of single stranded DNA. (FIG. 6).

Example 2. Preparing and Sequencing a Circular Single Stranded PCR-Amplified Library Sequencing libraries were prepared according to the method shown in FIG. 2 from 500 ng or 1 ug of *E. coli* genomic DNA. The library included the adaptor specific for the Pacific BioSciences RSII sequencing platform. Adapted nucleic acids were amplified with one of the pairs of primers from Table 1.

TABLE 1

| SEQ ID NO: 1 | forward | AACGGAGGAGGAGGAAAAG |
| --- | --- | --- |
| SEQ ID NO: 2 | reverse | /5phos/G*T*T*G*TTGT TGAGAGAGATT |
| SEQ ID NO: 3 | forward | GTTGTTGTTGAGAGAGATT |
| SEQ ID NO: 4 | reverse | /5phos/AACGGAGGAGGA GGAAAAG |

*- phosphorothioate nucleotide
/5phos/- 5'-phosphate

SEQ ID NO: 2 incorporated four phosphothioate nucleotides to confer T7 exonuclease resistance to the strand resulting from primer extension. SEQ ID NO: 4 incorporated a 5'-phosphate to facilitate digestion with Lambda exonuclease to the strand resulting from primer extension. Amplification products were treated with either T7 or Lambda exonucleases (depending on primers). DNA yield is shown in Table 2.

TABLE 2

| Exonuclease | Units | dsDNA yield (ng) | ssDNA yield (ng) |
| --- | --- | --- | --- |
| T7 exo | 10 U | 45.39 | 102.2 |
| T7 exo | 5 U | 43.01 | 98.7 |
| T7 exo | 1 U | 583.1 | 1311.8 |
| Lambda exo | 2.5 U | 46.92 | 101.5 |
| Lambda exo | 1 U | 59.16 | 116.2 |
| Lambda exo | 0.5 U | 85 | 130.9 |

The resulting libraries were sequenced on the RSII platform. The results are shown on FIG. 7 (T7 exonuclease) and FIG. 8 (Lambda exonuclease).

The combined results of Example 1 and Example 2 are summarized in Table 3.

TABLE 3

| | Percentage | | |
| --- | --- | --- | --- |
| | Single pass* | double stranded | Total single stranded circles** |
| Control (hairpin library) | 9 | 90 | 1 |
| Modification where one primer confers protection to one strand | 28 | 6 | 66 |
| Modification where one primer promotes digestion of one strand | 32 | 10 | 58 |
| Heat denature | 15 | 24 | 61 |

*"Single pass" are discarded reads that either do not align to the reference or lack an adapter sequence.
**Total single strand consists of (+) and (−) strands in equal amounts.

The invention claimed is:

1. A method of separately sequencing each strand of a double-stranded target nucleic acid, wherein the method comprises the following steps:
   (a) in a reaction mixture, joining a double-stranded target nucleic acid to an adaptor to form an adapted target nucleic acid, wherein the adaptor comprises primer-binding sites, and wherein the adaptor does not consist of a long strand and a short strand;
   (b) amplifying the adapted target nucleic acid with a pair of primers, wherein the pair of primers are complementary to the primer-binding sites, thereby forming an amplicon, wherein one primer in the pair of primers comprises a modified nucleotide affecting a rate of digestion by an exonuclease;
   (c) contacting the reaction mixture with an exonuclease, thereby eliminating from the reaction mixture the first of the two complementary strands of the amplicon;
   (d) circularizing the second of the two complementary strands of the amplicon to form a single stranded circle;
   (e) annealing a sequencing primer to the single-stranded circle; and
   (f) extending the primer, thereby sequencing one strand of the target nucleic acid.

2. The method of claim 1, wherein the joining of the double-stranded target nucleic acid to the adaptor is by ligation.

3. The method of claim 2, wherein the ligation is by joining of cohesive ends of the target nucleic acid and the adaptor.

4. The method of claim 1, wherein the adaptor comprises a double-stranded part and a single-stranded part comprising two non-annealed portions.

5. The method of claim 1, wherein the adaptor comprises at least one barcode.

6. The method of claim 1, wherein the modified nucleotide is a 5'-phosphorylated terminal nucleotide and the exonuclease is Lambda exonuclease.

7. The method of claim 1, further comprising a second exonuclease digestion step, after the circularization step (d).

8. The method of claim 1, wherein circularization is by splint ligation.

9. The method of claim 1, wherein the sequencing primer-binding site is in the adaptor.

10. The method of claim 1, further comprising, prior to step (c), contacting the reaction mixture with a DNA damage-specific agent selected from glycosylase and endonuclease.

11. The method of claim 1, wherein the steps (a)-(f) are performed on a plurality of target nucleic acids in a sample thereby forming and sequencing a library of nucleic acids from the sample.

* * * * *